US006652260B2

(12) United States Patent  
Nelson et al.

(10) Patent No.: US 6,652,260 B2
(45) Date of Patent: Nov. 25, 2003

(54) COMPOSITE ALLOGRAFT PRESS

(75) Inventors: Carl Nelson, Little Rock, AR (US); J. Marcus Hollis, Milton, FL (US); Charlene Flahiff, Durham, NC (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 319 days.

(21) Appl. No.: 09/879,564

(22) Filed: Jun. 12, 2001

(65) Prior Publication Data

US 2002/0025358 A1 Feb. 28, 2002

Related U.S. Application Data

(60) Continuation-in-part of application No. 09/343,135, filed on Jun. 29, 1999, now Pat. No. 6,293,971, which is a continuation of application No. 09/121,938, filed on Jul. 24, 1998, now Pat. No. 5,981,828, which is a division of application No. 08/647,424, filed on Mar. 11, 1996, now Pat. No. 5,824,078.

(51) Int. Cl.[7] .............................................. B29C 43/50
(52) U.S. Cl. ....................... 425/398; 425/408; 425/422; 425/436 R; 425/436 RM
(58) Field of Search ............................... 425/398, 403.1, 425/408, 422, 436 R, 438, 412, 443, 451.7, 436 RM

(56) References Cited

U.S. PATENT DOCUMENTS

| 3,686,922 A | 8/1972 | Bley .......................... 100/288 |
| 3,741,706 A | 6/1973 | Conley et al. .............. 425/406 |
| 3,786,676 A | 1/1974 | Korolyshun et al. ........... 73/94 |
| 4,284,400 A | * 8/1981 | Kaspar et al. ............... 425/398 |
| 4,678,470 A | 7/1987 | Nashef et al. ................. 623/16 |
| 4,904,265 A | 2/1990 | MacCollum et al. .......... 623/22 |
| 5,133,771 A | 7/1992 | Duncan et al. ............... 623/23 |
| 5,176,711 A | 1/1993 | Grimes ........................ 623/22 |
| 5,326,368 A | 7/1994 | Collazo ........................ 623/22 |
| 5,329,846 A | 7/1994 | Bonutti ......................... 100/50 |
| 5,372,492 A | * 12/1994 | Yamauchi ............... 425/436 R |
| 5,419,245 A | * 5/1995 | Short .......................... 100/289 |
| 5,507,813 A | 4/1996 | Dowd et al. .................. 623/16 |
| 5,549,699 A | 8/1996 | MacMahon et al. .......... 623/22 |
| 5,658,338 A | 8/1997 | Tullos et al. .................. 623/18 |
| 5,662,710 A | 9/1997 | Bonutti ........................ 623/11 |
| 5,665,121 A | 9/1997 | Gie et al. ..................... 623/16 |
| 5,769,897 A | 6/1998 | Harle .......................... 623/16 |
| 5,888,219 A | 3/1999 | Bonutti ........................ 623/11 |
| 6,132,472 A | 10/2000 | Bonutti ................... 623/23.72 |
| 6,206,676 B1 | * 3/2001 | McNally .................. 425/451.7 |

OTHER PUBLICATIONS

McCollum et al., "Bone–Grafting in Total Hip Replacement for Acetabular Protrusion," J. Bone & Joint Surg., Oct. 1980, vol. 62 (No. 7), pp. 1065–1073.

Slooff et al., "Bone Grafting in Total Hip Replacement for Acetabular Protrusion," Acta Orthop. Scand., Jun. 1984, vol. n/a (No. 55), pp. 593–596.

Gie et al., "Impacted Cancellous Allografts and Cement for Revision Total Hip Arthroplasty," J. Bone & Joint Surg, Jan. 1993, vol. 75 (No. 1), pp. 14–21.

* cited by examiner

Primary Examiner—Robert Davis
Assistant Examiner—Thu Khanh T. Nguyen
(74) Attorney, Agent, or Firm—J. Charles Dougherty

(57) ABSTRACT

A press to form a composite acetabular allograft cup for use in hip replacement surgery is disclosed. The acetabular cup formed by the press comprises bone cement and cancellous bone chips. The press includes a two-piece mold for forming the acetabular cup. The mold is removable from the press and may be available in many different sizes to accommodate a range of patients. A screw-type compression means is utilized to force the acetabular cup into the desired shape. A compression gauge allows the operator to monitor the pressure applied as the acetabular cup is formed to prevent excessive crushing of cancellous bone chips. Breaking jaws are used to separate the acetabular cup from the upper portion of the mold after the bone cement has set and the acetabular cup is formed.

15 Claims, 4 Drawing Sheets

COMPOSITE ALLOGRAFT PRESS

This application is a continuation-in-part of U.S. application Ser. No. 09/343,135, filed Jun. 29, 1999, now U.S. Pat. No. 6,293,971, which was in turn a continuation of U.S. application Ser. No. 09/121,938, filed Jul. 24, 1998, now U.S. Pat. No. 5,981,828, which was in turn a divisional of U.S. application Ser. No. 08/647,424, filed Mar. 11, 1996, now U.S. Pat. No. 5,824,078.

BACKGROUND OF THE INVENTION

The present invention relates to a press for forming composite allografts used in orthopedic surgery, and in particular to a press for forming composite acetabular allograft cups.

There is a need for methods of replacing or strengthening certain types of bone defects. One common example of such need applies in the case of hip replacement surgery. A hip joint is a ball and socket joint in which the ball is the femoral head and the socket is called the acetabulum (due to its supposed resemblance to a vinegar cruet). The cavity of the acetabulum is formed from three parts of the pelvic bone: above by the ilium, behind and below by the ischium, and internally by the os pubis. Patients who are otherwise candidates for hip replacement surgery may have acetabular defects. The acetabulum may for various reasons, including disease, trauma or prior surgery, contain defects such as missing or eroded portions of the acetabular wall. These defects must be corrected or compensated for if the surgery is to be successful.

In hip replacement surgery, a hip joint prosthesis, comprising a femoral component and an acetabular component, is employed to replace the femoral head and the acetabulum. The acetabular component may include a hemispherical metal cup or ring and a low-friction plastic liner of ultra-high molecular weight polyethylene. The procedure may also be done without the metal cup, using only the liner which is cemented in place.

One method of compensating for an acetabular defect is to repair the defect with a bone graft (either an allograft, typically harvested from a cadaver, or an autograft from the patient's own bone tissue). Due to the significant weight-bearing role of the hip joint, the stability and strength of the bone graft is a major concern. Metallic support cups may be required to support the bone graft material as disclosed in MacCollum (U.S. Pat. No. 4,904,265). MacCollum discloses a support cup in the shape of a rigid metallic hemisphere with a flange to support the bone graft. The outer surface of the support cup is disclosed to be porous to support bone ingrowth. A bearing insert of low-friction material for receiving the ball of the femoral prosthesis is mounted within the support cup.

As an alternative to bone grafts, Grimes (U.S. Pat. No. 5,176,711) discloses an acetabular hip prosthesis in which the acetabular component of the prosthesis includes an augmentation piece to fill a rim or cavitary defect. Likewise, Collazo (U.S. Pat. No. 5,326,368) discloses a modular prosthetic acetabular cup to provide various cross sections as desired to fill acetabular defects.

Another method of remedying an acetabular defect is disclosed in "Bone Grafting in Total Hip Replacement for Acetabular Protrusion" by McCollum, et al., *Journal of Bone and Joint Surgery*, Vol. 62-A, No. 7, 1065–1073 (October 1980). The McCollum article discloses the use of wafers of bone to fill a defect in the acetabular wall.

A slightly different technique is disclosed in "Bone Grafting in Total Hip Replacement for Acetabular Protrusion" by Slooff, et al., *Acta Orthop. Scand*, 55, 593–596, (1984). While Slooff et al disclose the use of a bone graft to close an acetabular defect, Slooff et al. also disclose surrounding the graft with a wall of cancellous bone chips that are molded and impacted by using the socket trial prosthesis. (Cancellous bone has a spongy or lattice-like structure and may be derived from cadaverous bone tissue such as femoral heads.) Slooff et al. disclose a technique of repairing an acetabular defect in which cancellous bone chips are molded and impacted around a bone graft, but do not disclose the addition of cement to the impacted bone chips.

Gie, et al. in "Impacted Cancellous Allografts and Cement for Revision Total Hip Arthroplasty," *The Journal of Bone and Joint Surgery*, Vol. 75-B, No. 1, 14–21 (January 1973) disclose the use of impacted cancellous allografts and cement for fixation of the femoral component in total hip arthroplasty. The technique disclosed by Gie et al. involves packing allograft bone chips into the femoral canal using the trial femoral component. The chips are repeatedly impacted after which cement is introduced and pressurized to force the cement into the graft. Pressure is maintained until the cement has sufficiently solidified. While Gie et al. disclose impacting cancellous bone chips into the femoral canal after which cement is added to the impacted bone chips and pressurized to force the cement into the graft, Gie et al. do not disclose the use of this technique in relation to the acetabulum. Neither Slooff et al. nor Gie et al. disclose the formation of a composite acetabular cup outside the body of the patient prior to surgery.

It is known to form human tissue into particular shapes to create desired natural tissue grafts. For example, U.S. Pat. No. 4,678,470 issued to Nashef et al. on Jul. 7, 1987 for "Bone-Grafting Material" discloses a bone-grafting material derived from allogenic or xenogenic bone that may be machined into a predetermined shape.

U.S. Pat. No. 5,329,846 issued to Bonutti on Jul. 19, 1994 for "Tissue Press and System" discloses a press for shaping or compressing a piece of tissue by the movement of two members relative to each other. Various shapes of the two movable members may be selected so as to produce tissue in the desired shape. While the Bonutti invention is primarily directed to the compression and shaping of soft tissue, portions of the disclosure suggest the shaping of bone tissue with the addition of polymeric material (column 11, lines 11–13). Bonutti does not expressly disclose the formation of an acetabular cup using cancellous bone chips and cement. While Bonutti discloses the importance of monitoring and controlling the pressure applied to the compressed tissue, it is in the context of maintaining graft tissue in a living state to improve graft viability and tissue healing. In this context Bonutti discloses the use of pressure sensors and force-limiting means such as the mechanism found on torque wrenches. (See FIG. 6A.)

It is known to use pressure gauges, load limiting devices and the like in presses in the manufacturing environment. An example is U.S. Pat. No. 3,786,676 which discloses a compression testing machine having an in-line load cell.

SUMMARY OF THE INVENTION

The present invention is directed to a press for forming a composite acetabular allograft cup. The acetabular allograft press comprises a base and upper frame that are forced together to apply pressure to a two-piece mold in the shape of the required acetabular cup. Various sizes of molds may be employed for different patient requirements. Pressure is applied by a manually operated screw mechanism. A pressure gauge is used to indicate the correct degree of loading to the mold.

One potential problem with the use of a press is that the operator may have difficulty removing the allograft cup from the mold after it has set, since the bone cement used in forming the acetabular cup may adhere to the upper portion of the mold. To overcome this problem, the present invention includes breaking jaws that extend between the upper portion of the mold and the allograft cup when the mold is closed during acetabular cup formation. To separate the allograft cup from the upper portion of the mold, the operator merely presses down firmly on the handle mechanically linked to the breaking jaws. This forces the cup down and away from the upper portion of the cup, with a sufficient degree of force to break the bond between the acetabular cup and the upper portion of the mold.

The method of using the acetabular allograft press comprises the following steps:

(a) a quantity of cancellous bone chips is placed in the mold (cancellous bone chips are commercially available);

(b) pressure is applied to the bone chips to cause the chips to conform to the shape of the mold (it is important that the load applied to the bone chips is limited to avoid excessive crushing of the bone);

(c) the mold is opened and additional bone chips are added to fill any voids;

(d) a load is again placed on the bone chips to cause the newly added bone chips to conform to the shape of the mold;

(e) commercially available bone cement is added to the mold;

(f) the mold is again loaded and the load is maintained for a sufficient period of time for the cement to harden; and (g) the allograft cup is separated from the upper portion of the mold using the breaking jaws so that the acetabular cup can be removed.

This process produces a synthetic composite acetabular cup in which the inner surface is smooth and comprised essentially of hardened bone cement material. The outer portion of the cup may have a limited proportion of cement extrusions but the major portion of the exterior of the cup shows exposed cancellous bone surface. The acetabular cup is therefore suited to provide a smooth, strong inner surface to receive an acetabular implant, while the outer surface is suited for encouraging bone growth from the acetabulum into the exposed bone of the acetabular cup. While this technique is disclosed with reference to the particular application of an acetabular cup, the same techniques offer advantages in other applications where an allograft having the described properties is desirable. The present invention should not, therefore, be seen as limited to one particular application.

In surgery, the acetabular cup is highly advantageous since it avoids the necessity of performing grafting to correct acetabular defects such as by the method disclosed in Gie et al. The acetabular cup made using the press of the present invention could be formed in advance of surgery. During surgery the acetabular cup is positioned in the acetabulum so as to fill the acetabular defect and fixed in place using screws. The remainder of the total hip replacement surgery would be carried out using well-known techniques. Using the surgical method of the present invention, however, a metal acetabular cup component is not required. A high-density plastic liner is affixed with bone cement directly to the synthetic composite acetabular cup to receive the femoral component. The use of the present invention is not limited to the acetabulum; the press could also be used to form synthetic allografts for other purposes in orthopedic surgery that would be apparent to one skilled in the art.

It is therefore an object of the present invention to provide for a press to form a synthetic composite allograft.

It is also an object of the present invention to provide for a press to form a synthetic composite acetabular cup for the repair of acetabular defects encountered in total hip replacement surgery.

It is a further object of the present invention to provide for a press to form synthetic composite allografts, and in particular a synthetic composite acetabular cup, which presents a smooth, strong inner surface of hardened cement material and an outer surface consisting essentially of compacted cancellous bone chips.

It is a further object of the present invention to provide for a press with a screw-type mechanism that includes breaking jaws so that the allograft cup may be easily separated from the mold and removed after the cup is formed.

Further objects and advantages of the present invention will become apparent from an examination of the detailed description of the preferred embodiments considered in conjunction with the appended drawings as described hereinafter.

DETAILED DESCRIPTION OF THE PREFERRED EMBODIMENT

Figure 1:
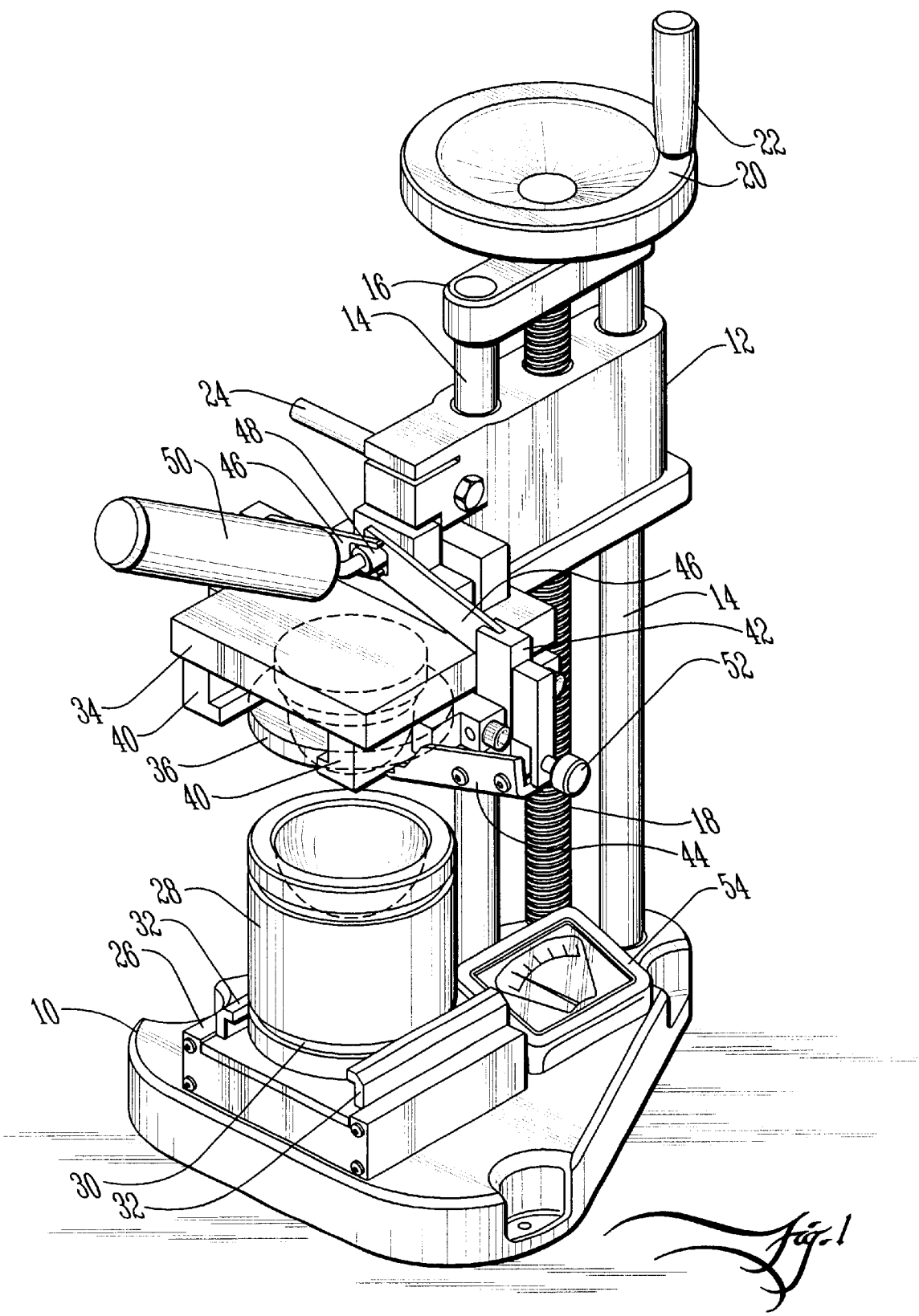
FIG. 1 is a perspective view of the press for producing an acetabular cup.
Figure 2:
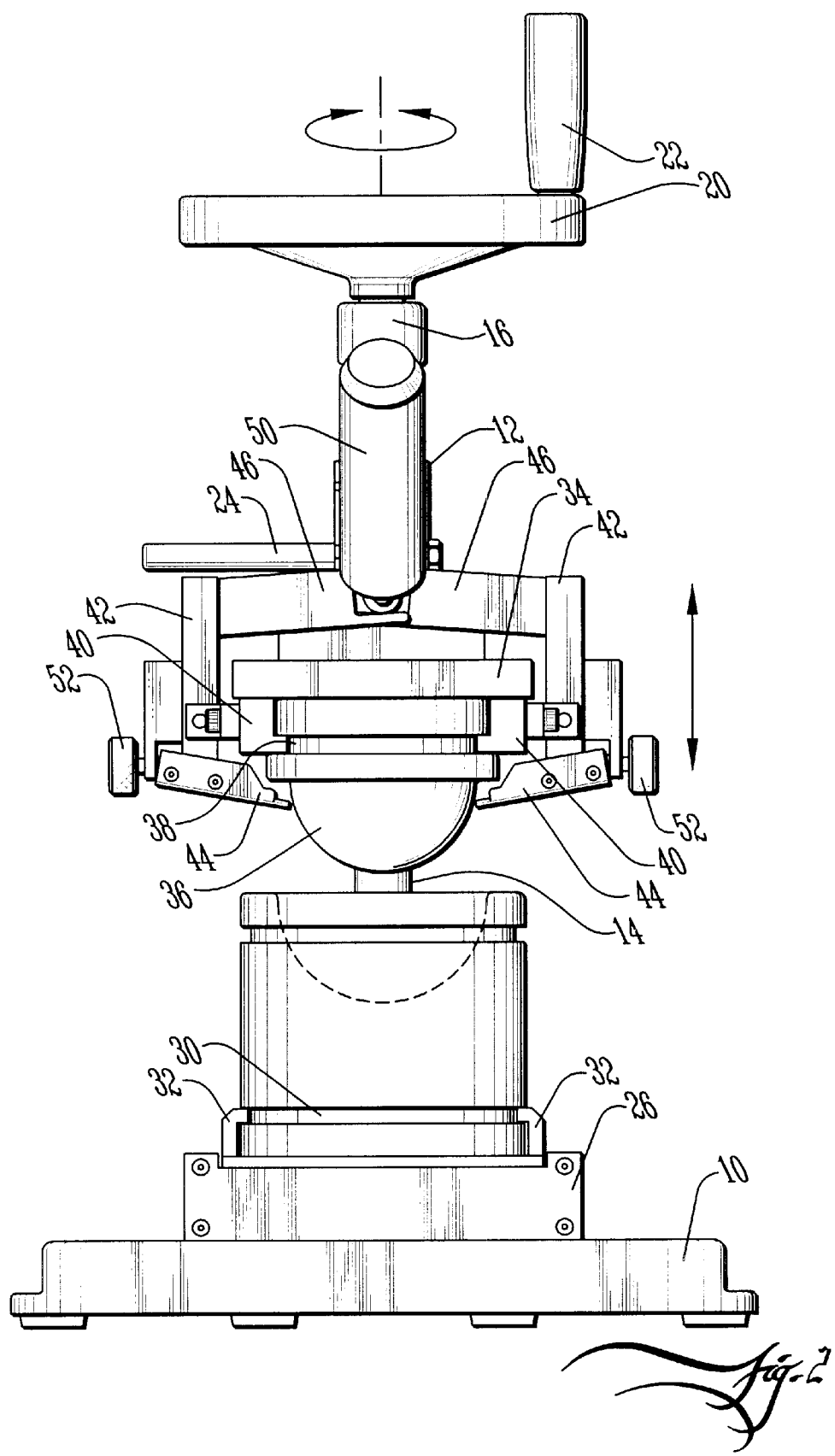
FIG. 2 is a front elevational view of the press for producing an acetabular cup.
Figure 3:
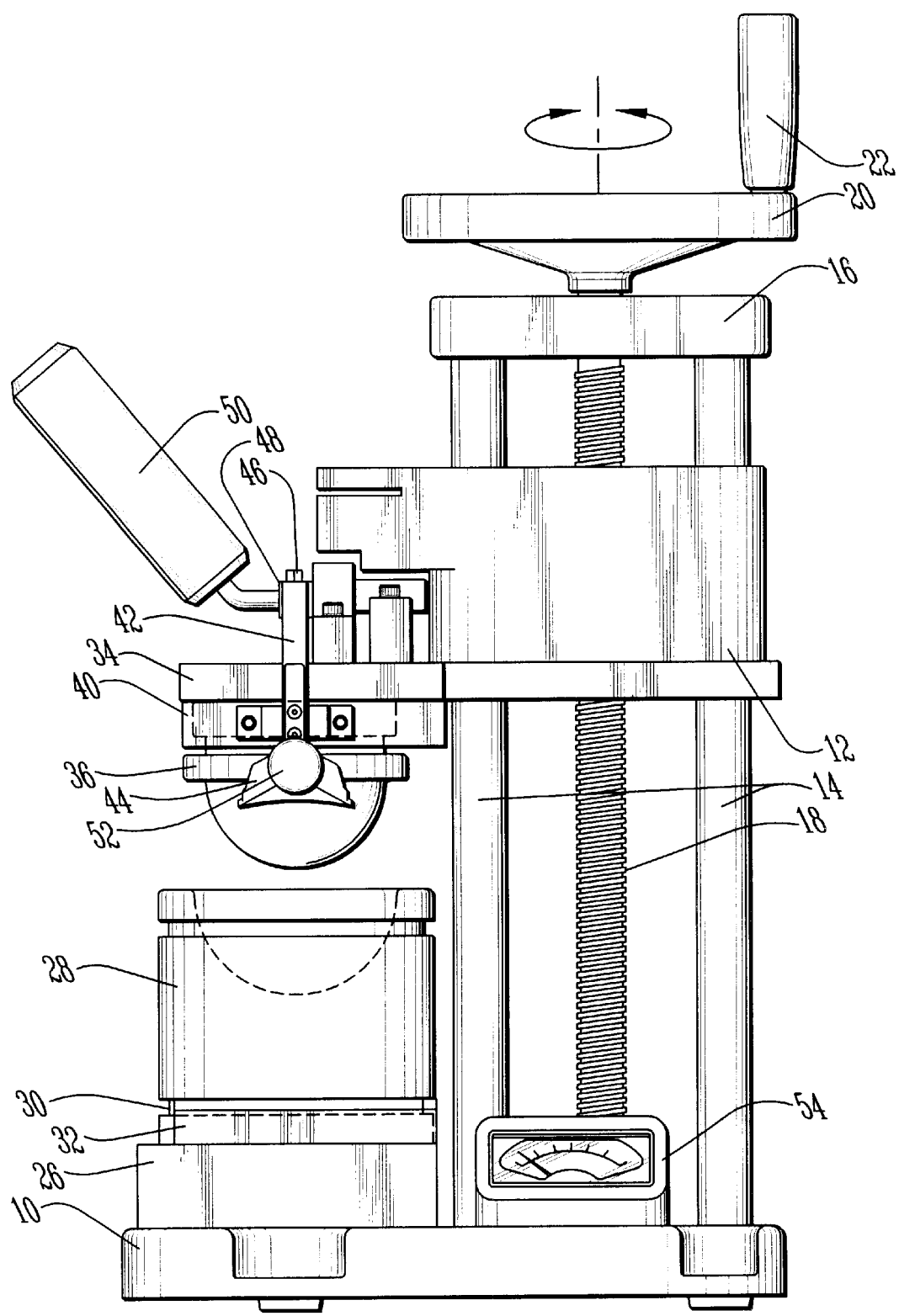
FIG. 3 is a side elevational view of the press for producing an acetabular cup.

The press of the present invention may be described generally with reference to FIGS. 1–3. The main components of the press are mounted on base 10. Upper frame 12 is linearly movable with respect to base 10 by sliding up or down along guide rods 14. Guide rod cap 16 serves as a stop to prevent upper frame 12 from traveling upward beyond a desired height. Guide rods 14 must be long enough that when the press is in the fully open position the operator may easily install and remove the acetabular cup mold portions, as described below.

Screw 18 is mounted between base 10 and guide rod cap 16 such that it may rotate freely about its axis. The upper end of screw 18 extends through and beyond guide rod cap 16 and receives screw wheel 20. Screw wheel 20 lies above guide rod cap 16 in a plane parallel to that of base 10. Screw 18 and screw wheel 20 are rigidly connected together using means as are known in the art such that the rotation of screw wheel 20 will cause screw 18 to rotate about its axis without slippage. Screw wheel handle 22 is mounted on the face of screw wheel 20 near an edge, such that an operator may cause screw 20 to rotate on its axis by gripping screw wheel handle 22 and moving his or her hand in a circular motion.

Screw 18 passes through upper frame 12 within a threaded passage sized to receive screw 18, such that the rotation of screw 18 causes upper frame 12 to rise or fall relative to base 10 along guide rods 14. Preferably, clockwise rotation of screw 18 causes upper frame 12 to move closer to base 10 and counterclockwise rotation of screw 18 causes upper frame 12 to move closer to guide rod cap 16. Upper frame 12 may be locked in place by twisting upper frame lock handle 24, thereby causing upper frame lock (not shown within upper frame 12) to press tightly against one of guide rods 14. Because of the threaded fit between upper frame 12 and screw 18, screw 18 cannot rotate when upper frame 12 is locked into place.

Mounted on top of base 10 is lower mold plate 26. Lower mold plate 26 is large enough such that lower mold 28 may be fitted entirely on top of it. Lower mold 28 is preferably of cylindrical shape, with a hemispherical dome-shaped section removed from its top, thereby forming the lower portion of a mold for forming a composite allograft cup. Lower mold groove 30 is sized to receive lower mold flanges 32, which are mounted to lower mold plate 26 and serve to hold lower mold 28 in place against lower mold plate 26 as the press is used.

Mounted to upper frame 12 is upper mold plate 34. Upper mold 36 is preferably of cylindrical shape, with a hemispherical dome-shaped section extending from its lower portion, thereby forming the upper portion of a mold for forming a composite allograft cup. Upper mold groove 38 is sized to receive upper mold flanges 40, which are mounted to upper mold plate 34 and serve to hold upper mold 36 in place against upper mold plate 34 as the press is used.

In the preferred embodiment, various lower molds 28 and upper molds 36 of different sizes may be employed with the press. Each of the lower molds 28 and upper molds 36 are cut in pairs, designed to fit together to form an allograft cup of a particular size. The exterior of each lower mold 28 and upper mold 36 should be of the same size, such that each fits into lower mold flanges 32 and upper mold flanges 40, respectively. In this way a composite allograft cup of various sizes may be formed by simply replacing lower mold 28 and upper mold 36. This design allows the simple construction of allograft cups of various sizes as correspond to each particular patient, provided that a sufficient number of molds are available in various sizes such that the size required for any given patient may be accommodated. For example, a series of molds with diameters from 60 to 70 millimeters at 2 millimeter increments would be adequate for most purposes.

While the drawing figures illustrate a lower mold 28 and upper mold 36 shape having a smooth inner surface, the scope of the present invention is not so limited. A shape having ridges or some other form of textured surface may have advantages in some applications. Any predetermined shape that can be formed by a two-piece mold is suitable for the practice of the present invention.

Breaking jaw mounts 42 are attached to either side of upper mold plate 34. Breaking jaws 44 are hingeably attached at breaking jaw mounts 44 and extend below upper mold plate 34. Breaking jaws 44 engage upper mold 36 when upper mold 36 is in the press by extending below a portion of upper mold 36. A portion of breaking jaws 44 thus extends between lower mold 28 and upper mold 36 when upper mold 36 and lower mold 28 are brought together as an allograft press is formed.

Breaking jaws 44 are mechanically linked to breaking jaw arms 46, which extend across the top of upper mold plate 34. Breaking jaw handle mount 48 is attached to the top of upper mold plate 34, with breaking jaw handle 50 extending from the front side of breaking jaw handle mount 48. The ends of breaking jaw arms 46 opposite from the mounting point at breaking jaw mounts 42 meet at breaking jaw handle 50. Breaking jaw handle 50, breaking jaw arms 46, and breaking jaws 44 are linked such that downward pressure on breaking jaw handle 50 serves to force breaking jaws 44 downward, thereby pushing upper mold 36 away from lower mold 28 when the two are in contact as an allograft cup is being formed. Breaking jaw knobs 52 may be turned to adjust the tension on breaking jaws 44 in a manner well known in the art.

Compression gauge 54 is mounted to base 10 adjacent to lower mold plate 26. Compression gauge 54 is coupled to lower mold plate 26 in such a manner as is well known in the art such that the pressure applied between upper mold 36 and lower mold 28 may be measured by compression gauge 54. Although in the preferred embodiment compression gauge 54 utilizes a standard needle-type display, any other of the well-known types of gauge displays could also be utilized with the present invention.

Figure 4:
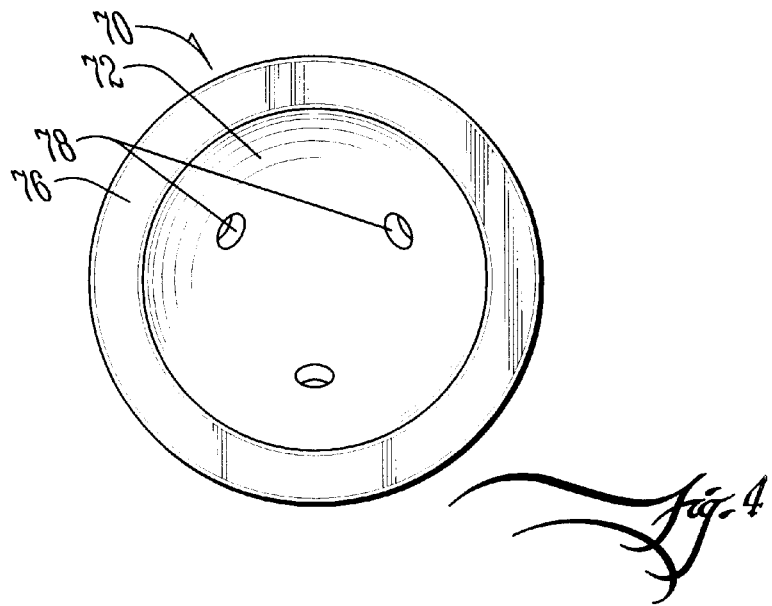
FIG. 4 is a plan view of the inner surface of the acetabular cup.
Figure 5:
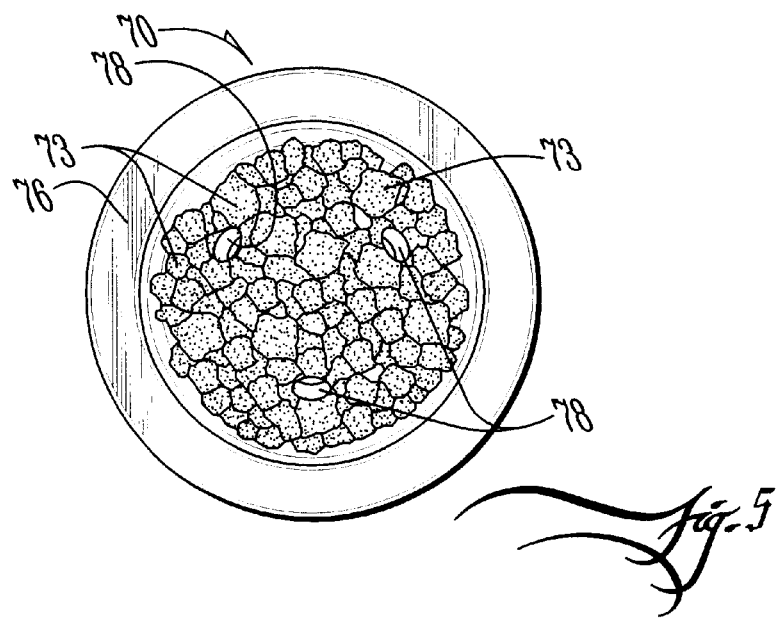
FIG. 5 is a plan view of the outer surface of the acetabular cup.
Figure 6:
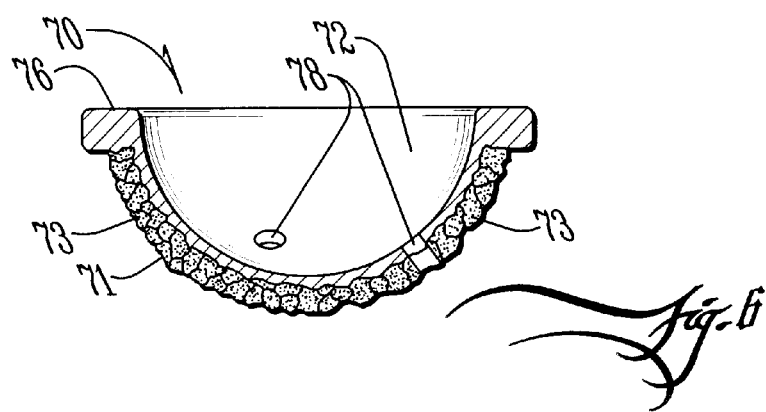
FIG. 6 is a cross-section view of the acetabular cup.

The use of the composite allograft press described above may now be described with reference to FIGS. 1–6. First, a lower mold 28 and upper mold 36 is made to a predetermined shape as appropriate for the particular allograft application. In the particular case of a composite allograft used to repair defects in the acetabular wall, an acetabular cup 70 in the shape of a hollow hemispherical dome, as shown in FIGS. 4–6, is desirable. Accordingly, FIGS. 1–3 show a lower mold 28 having a hemispherical shape appropriate to the outer surface 71 of the acetabular cup 70 and an upper mold 36, likewise having a similar hemispherical shape although of a smaller radius, so that the combination produces a hollow hemispherical dome sized to fit within the patient's acetabulum. As shown in FIG. 4, the hollow hemispherical dome of the composite acetabular allograft cup 70 further has an inner surface 72 sized to receive the other components required in total hip replacement.

In order to form a composite allograft, a quantity of cancellous bone chips 73 is placed in lower mold 28. Cancellous bone chips are derived from cadaverous bone and are characterized by a spongy or lattice-like structure. The cancellous bone chips 73 have the property of encouraging and accepting bone ingrowth from the defective acetabulum. Cancellous bone chips are commercially available. A size of one cubic centimeter is optimum for the practice of the invention, although a range of sizes above and below the optimum would be acceptable.

Lower mold 28 is then loaded into the press by sliding lower mold 28 across lower mold plate 26 with lower mold flanges 32 fitted into lower mold groove 30. Likewise, the corresponding upper mold 36 is loaded into the press by sliding upper mold 36 against upper mold plate 34 with upper mold flanges 40 fitted into upper mold groove 38.

To place a load onto cancellous bone chips 73, the operator may manipulate screw wheel handle 22 such that screw wheel 20 rotates in a clockwise direction, thereby rotating screw 18 in a clockwise direction and causing upper frame 12 to move toward base 10. The lowering of upper frame 12 causes the hemispherical portion of upper mold 36 to extend downward into lower mold 28, thereby contacting cancellous bone chips 73 within lower mold 28. The load applied to the cancellous bone chips 73 is for the purpose of conforming cancellous bone chips 73 to the shape of lower mold 28. A minor amount of crushing of cancellous bone chips 73 is acceptable and may even be desirable to assist in forming a compact and somewhat consolidated mass. However, excessive crushing of the bone chips could lead to the closing off of the lattice-like structure of cancellous bone chips 73 so as to interfere with the desirable ingrowth of bone from the acetabulum once acetabular cup 70 is implanted. Therefore, the operator may rely on compression gauge 54 to avoid the application of excessive loads to cancellous bone chips 73. The optimum range of loads is from about 250 to about 500 pounds. Loads of 1000 pounds or above should be avoided.

After conforming and consolidating cancellous bone chips 73, the mold is opened by manipulating screw wheel handle 22 such that screw wheel 20 and screw 18 rotate counterclockwise, thereby moving upper mold 36 away from and out of lower mold 28. The consolidated cancellous bone chips 73 may now be inspected for voids. If any voids are present, additional cancellous bone chips 73 may be added to lower mold 28. A load is then reapplied to consolidate the newly added cancellous bone chips 73. This process may be repeated as often as necessary to fill and consolidate any voids in the mass of cancellous bone chips 73 in lower mold 28.

Once the cancellous bone chips 73 have been consolidated and conformed to the lower mold 28 so as to form the desired outer surface 71 without significant voids, a quantity of commercially available bone cement is added to lower mold 28. The bone cement will typically be a methyl methacrylate type. A load is then reapplied so as to cause the newly added bone cement to conform to upper mold 36 so as to form the desired inner surface 72 of acetabular cup 70. The load is maintained for a sufficient period of time for the bone cement to harden. The amount of time required for the bone cement to harden depends on the particular type of cement used and other environmental conditions. For commercially available methyl methacrylate bone cement, the setting time will be approximately eight minutes. To hold the press in position with the appropriate compression during this time, upper mold 36 is locked in place by twisting upper frame lock handle 24.

Once the bone cement has set, the now-formed acetabular cup 70 (shown in FIGS. 4–6) will be stuck to upper mold 36. To separate acetabular cup 70 from upper mold 36, the operator may depress breaking jaw handle 50, which serves to press breaking jaws 44 downward due to the mechanical linkage between breaking jaw handle 50, breaking jaw arms 46, and breaking jaws 44. The movement of breaking jaws 44 serves to force acetabular cup 70 down and away from upper mold 36 so that acetabular cup 70 separates from upper mold 36. The press may then be fully opened by manipulating screw wheel handle 22 such that screw wheel 20 and screw 18 turn counterclockwise, thereby raising upper frame 12. Lower mold 28 may then be removed from the press in order for the operator to gain easy access to acetabular cup 70.

The action of upper mold 36 pressing against the bone cement causes the bone cement to flow around upper mold 36 so as to form an inner surface 72 conforming to the shape of the upper mold 36 and consisting essentially of hardened bone cement. The surface 72 is thus a smooth, uniform hardened surface. Due to the partially consolidated nature of the cancellous bone chips 73, however, the bone cement only penetrates the partially consolidated mass of cancellous bone chips 73 to a limited extent. While limited extrusions of hardened bone cement may appear on outer surface 71, outer surface 71 will consist essentially of the exposed surface of cancellous bone chips 73. Outer surface 71 is thus of the appropriate shape to be received in the acetabulum of the patient and further presents a surface of exposed cancellous bone chips 73, which is conducive to bone ingrowth from the acetabulum into the composite acetabular allograft cup 70.

While the shape of acetabular cup 70 is essentially that of a hollow hemispherical dome, it may be noted from FIGS. 4–6 that a rim 76 may easily be formed on acetabular cup 70. Such a rim 76 may be desirable in certain applications, while in other applications rim 76 is not required. The shape of lower mold 28 may be adjusted in order to form rim 76 on acetabular cup 70.

Acetabular cup 70 thus presents an outer surface 71 comprised essentially of exposed cancellous bone chips 73 with minimal extrusions of hardened bone cement and an inner surface 72 comprised essentially of hardened bone cement. For implantation of acetabular cup 70, holes 78 may be drilled through acetabular cup 70. In some applications holes 78 may be located in rim 76.

The preferred construction material for most of the components of the present invention is stainless steel. Stainless steel has the strength to withstand the pressures generated within the press during use without deformation, while also providing resistance to corrosion that may occur due to exposure to moisture or liquids in the laboratory environment. Stainless steel may be easily cleaned and sanitized, which is critical if the press is to be used at or near a location where surgery is to be performed. In the alternative, however, the molds of the present invention may be formed from a high-strength polymer instead of steel. Polymer molds have the advantage of relatively low cost, and thus the molds could be considered disposable. This would alleviate the need for cleaning between uses. Since a multitude of molds of different sizes is necessary in order to use the invention for a wide variety of patients, the use of polymer molds may significantly reduce the initial cost of the invention if a full set of molds is purchased.

The present invention has been described with reference to certain preferred and alternative embodiments which are intended to be exemplary only and not limiting to the full scope of the present invention as set forth in the appended claims.

What is claimed is:

1. A press for molding a composite allograft, the press comprising:

(a) a base;
   (b) a transverse upper frame movable relative to said base;
   (c) an upper mold attachable to said upper frame;
   (d) a lower mold attachable to said base;
   (e) compression means in communication with said upper frame and said base, and operable to apply a load between said upper mold and said lower mold; and
   (f) at least one breaking jaw wherein the composite allograft may be separated from said upper mold by manipulation of said breaking jaw.

2. The press of claim 1, wherein said compression means comprises screw means by which said upper frame may be linearly displaced relative to said base.

3. The press of claim 1, further comprising an upper frame lock wherein said upper frame may be locked into position relative to said base.

4. The press of claim 1, wherein said upper mold has a smooth, hemispherical shape.

5. The press of claim 4, wherein said lower mold has a smooth, bowl-like shape that is adapted to receive said upper mold.

6. The press of claim 5, wherein said upper mold and said lower mold are shaped to form an allograft in the shape of a hollow, hemispherical dome.

7. The press of claim 5, wherein said upper mold and said lower mold are shaped to form an allograft in the shape of a hollow, hemispherical dome having a rim extending outwards along the edge of the allograft.

8. A press for molding a composite allograft, comprising:
   (a) a base;
   (b) a transverse upper frame movable relative to said base;
   (c) a plurality of interchangeable upper molds, each said upper mold mountable onto said upper frame;
   (d) a plurality of interchangeable lower molds, each said lower mold mountable onto said base and shaped so as to receive one of said upper molds when mounted onto said upper frame;
   (e) compression means for applying a load between that one of said upper molds that is mounted to said upper frame and that one of said lower molds that is mounted to said base; and
   (f) at least one breaking jaw wherein the composite allograft may be separated from that one of said upper molds that is mounted to said upper frame by manipulation of said breaking jaw.

9. The press of claim 8, further comprising an upper frame lock wherein said upper frame may be locked into position relative to said base.

10. The press of claim 8, further comprising a compression gauge operable to measure the compression load between that one of said upper molds that is mounted to said upper frame and that one of said lower molds that is mounted to said base.

11. The press of claim 8, wherein said compression means comprises screw means by which said upper frame may be linearly displaced relative to said base.

12. The press of claim 8, wherein said upper mold has a smooth, hemispherical shape.

13. The press of claim 12, wherein said lower mold has a smooth, bowl-like shape which is adapted to receive said upper mold.

14. The press of claim 13, wherein said upper mold and said lower mold are shaped to form an allograft in the shape of a hollow, hemispherical dome.

15. The press of claim 13, wherein said upper mold and said lower mold are shaped to form an allograft in the shape of a hollow, hemispherical dome having a rim extending outwards along the edge of the allograft.

* * * * *